(12) United States Patent
Molloy

(10) Patent No.: US 8,888,833 B2
(45) Date of Patent: Nov. 18, 2014

(54) DELIVERY SYSTEM HAVING ONE PIECE INNER MEMBER WITH FLAT DISTAL END PORTION

(75) Inventor: Shane Molloy, San Diego, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1158 days.

(21) Appl. No.: 12/271,538

(22) Filed: Nov. 14, 2008

(65) Prior Publication Data
US 2010/0125280 A1  May 20, 2010

(51) Int. Cl.
*A61F 2/06* (2013.01)
*A61F 2/95* (2013.01)
*A61F 2/966* (2013.01)

(52) U.S. Cl.
CPC . *A61F 2/95* (2013.01); *A61F 2/966* (2013.01); *A61F 2002/9517* (2013.01)
USPC ........................................ 623/1.11

(58) Field of Classification Search
USPC ............... 623/1.11, 1.12, 1.23; 606/108, 191, 606/194, 198, 200
See application file for complete search history.

(56) References Cited

U.S. PATENT DOCUMENTS

| | | | | | |
|---|---|---|---|---|---|
| 4,943,278 | A | * | 7/1990 | Euteneuer et al. | 606/194 |
| 5,549,553 | A | * | 8/1996 | Ressemann et al. | 604/103.08 |
| 5,938,623 | A | * | 8/1999 | Quiachon et al. | 600/585 |
| 6,120,476 | A | * | 9/2000 | Fung et al. | 604/95.04 |
| 2003/0187457 | A1 | * | 10/2003 | Weber | 606/110 |
| 2005/0113902 | A1 | * | 5/2005 | Geiser et al. | 623/1.11 |
| 2006/0247661 | A1 | * | 11/2006 | Richards et al. | 606/108 |
| 2009/0082843 | A1 | * | 3/2009 | Cox et al. | 623/1.11 |

* cited by examiner

*Primary Examiner* — Katherine M Shi
(74) *Attorney, Agent, or Firm* — Jonathan D Feuchtwang; Fulwider Patton LLP

(57) ABSTRACT

A delivery system has reduced profile in the catheter portion of the delivery system without compromising the pushability of the delivery system. The present invention also provides a structure which improves and simplifies the attachment of small catheter components to other structures forming the catheter portion the delivery system.

17 Claims, 9 Drawing Sheets

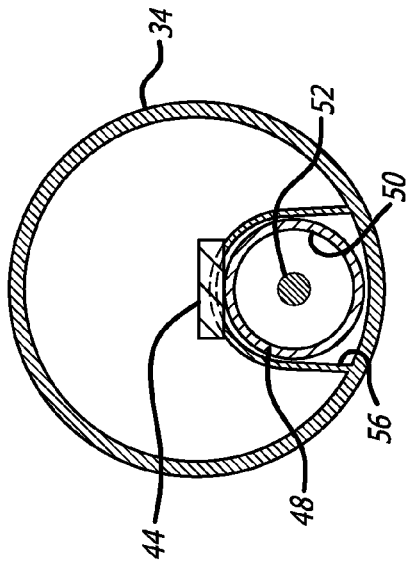
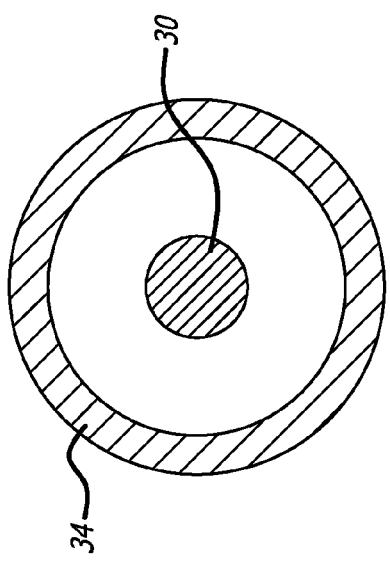
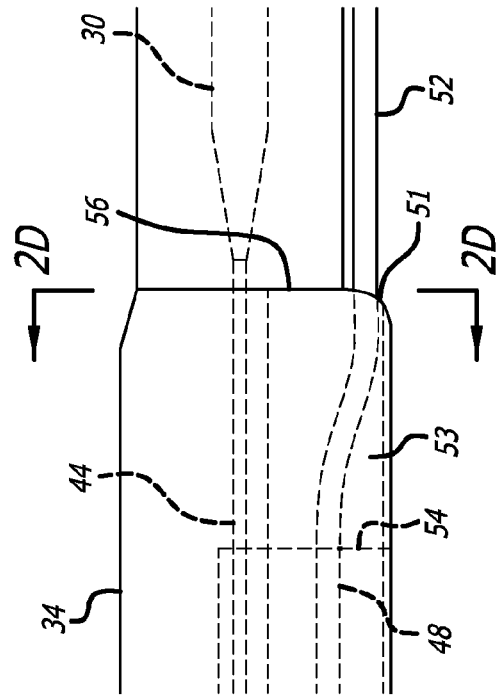

DELIVERY SYSTEM HAVING ONE PIECE INNER MEMBER WITH FLAT DISTAL END PORTION

BACKGROUND OF THE INVENTION

The present invention relates generally to delivery systems for deploying medical devices and, more particularly, to delivery systems to accurately deploy medical devices, such as a stent, a vascular stent-graft and the like, in a body vessel of a patient for the treatment of stenosis, aortic aneurysms and other afflictions which may strike body lumens.

Stents are generally cylindrically shaped devices which function to hold open and sometimes expand a segment of a blood vessel or other arterial lumen, such as coronary artery. Stents are usually delivered in a compressed condition to the target site and then deployed at that location into an expanded condition to support the vessel and help maintain it in an open position. They are particularly suitable for use to support and hold back a dissected arterial lining which can occlude the fluid passageway there through. Stents are particularly useful in the treatment and repair of blood vessels after a stenosis has been compressed by percutaneous transluminal coronary angioplasty, percutaneous transluminal angioplasty, or removed by atherectomy or other means, to help improve the results of the procedure and reduce the possibility of restenosis. Stents, or stent like devices, are often used as the support and mounting structure for implantable vascular grafts which can be used to create an artificial conduit to bypass the diseased portion of the vasculature, such as an abdominal aortic aneurism.

A variety of devices are known in the art for use as stents and have included coiled wires in a variety of patterns that are expanded after being placed intraluminally on a balloon catheter; helically wound coiled springs manufactured from an expandable heat sensitive metal; and self expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery and accommodate the often tortuous path of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self expanding stent formed from shape memory metals or super-elastic nickel titanium alloys, which will automatically expand from a compressed state when the stent is advanced out of the distal end of the delivery, or when a restraining sheath which holds the compressed stent in its delivery position is retracted to expose the stent.

Some prior art stent delivery systems for delivery and implanting self-expanding stents include an inner member upon which the compressed or collapsed stent is mounted and an outer restraining sheath which is initially placed over the compressed stent prior to deployment. When the stent is to be deployed in the body vessel, the outer sheath is moved in relation to the inner member to "uncover" the compressed stent, allowing the stent to move to its expanded condition. Some delivery systems utilize a "push pull" type technique in which the outer sheath is retracted while the inner member is pushed forward. Another common delivery system utilizes a simple pull back delivery system in which the self expanding stent is maintained in its compressed position by an outer sheath. Once the mounted stent has been moved at the desired treatment location, the outer sheath is pulled back via a deployment handle located at a remote position outside of the patient, which uncovers the stent to allow it to self expand within the patient. Still other delivery systems use an actuating wire attached to the outer sheath. When the actuating wire is pulled to retract the outer sheath and deploy the stent, the inner member must remain stationary, preventing the stent from moving axially within the body vessel.

In certain applications, it is desirable to employ a delivery system which provides a low profile to allow the catheter portion of the system to reach tight distal lesions. For such applications, the stent delivery catheter is required to have a relatively low profile to facilitate positioning the operative distal end portion of the catheter at the desired treatment site in the patient's body lumen. Delivery system can attain a reduced overall profile by utilizing tubular components having a small diameter to create the catheter portion of the delivery system. However, the delivery system will still require the use of components that provide sufficient pushability or axial stiffness to allow the catheter portion to be delivered over a guide wire to the target location. For example, a catheter with a distal shaft section having a large wall thickness likely has sufficient catheter tensile strength to be pushed along a guide wire to a target location in a patient's vasculature, however, it may not have sufficient flexibility and low profile/lumen size to be practicable in all applications. If the catheter shaft does not possess sufficient pushability, then the physician may have a difficult time reaching the target lesion. The catheter profile must be balanced with competing considerations such as the catheter tensile strength and kink resistance, and other important characteristics such as those related to the nature of the materials used to form the catheter components. When downsizing catheter components to reduce the overall profile of the catheter, the size of the components must still be strong enough to supply the pushability and kink resistance needed for a given application. Accordingly, while it is desirable to reduce the profile of a delivery system, the delivery system's pushability should not be compromised. Therefore, what has been needed is a stent delivery catheter system with an improved balance of these catheter characteristics.

Some delivery systems which utilize an inner catheter member to support or carry a medical device obtain the necessary axial strength by rely on lengths of tubing having different axial strengths. In this regard, the more proximal sections of the inner catheter member utilize tubing which has increased axial strength to allow the physician to push the catheter portion of the delivery system through the body vessel. The more distal section of the inner catheter member is usually made from a much more flexible tubing to provide needed flexibility at the distal end which often is placed in tortuous and narrow body vessels. As a result, the inner catheter member is often made from a number of different tubular sections bonded together to create a composite unit. From a manufacturing standpoint, the bonding of different tubular sections together increases the overall cost of the product since such bonding steps can often be labor intensive. Additionally, there is always a possibility that the catheter could tear as the physician is pulling the catheter from the patient.

The manufacturing of stent delivery systems also often require the physical attachment of small components together to create a composite catheter. For example, atraumatic catheter tips, often attached at the distal most end of the catheter portion of a delivery system, provide a soft component that helps to prevent trauma to the vessel walls as the catheter portion is being delivered through, for example, the patient's vasculature. Delivery systems that do not include a distal tip at the end of the catheter portion can cause a "snow-plowing" effect as the distal tip scrapes against the vessel walls. The scraping of the distal end of the catheter portion can cause significant damage to the vessel walls and could promote the formation of plaque at the damaged locations. Soft distal tips can prevent this from occurring and thus are quite useful to a stent delivery system or any delivery system which is delivered into a body vessel. However, the distal tip must remain permanently attached to the catheter portion. A catheter distal tip which becomes un-attached within the body lumen can cause extreme trouble to the physician performing the medical procedure. For example, a catheter design having insufficient tensile strength can result a catheter failure as the catheter is under tension while being proximally retracted from within the patient's body lumen, such that the catheter shaft partially or completely tears, which can result in the potentially lethal dislocation of the catheter distal tip. Therefore, there is also a need to maintain the distal tip permanently bonded to the catheter on any delivery system.

The present invention disclosed herein satisfies these and other needs.

SUMMARY OF THE INVENTION

Briefly and in general terms, the present invention is directed towards delivery systems and methods of their use for reducing the overall profile of the catheter portion of the delivery system without compromising the pushability of the delivery system. The present invention also provides a structure which improves and simplifies the attachment of small catheter components to other structures forming the catheter portion the delivery system.

In one particular embodiment, the delivery system utilizes an inner catheter member made from single wire having a distal flat wire portion that enhances the bonding of certain catheter components thereto. The use of a single, continuous wire for the inner portion also eliminates the need to bond various tubular components together to form a suitable inner member. The system includes a control handle and a catheter portion coupled to the control handle. The catheter portion including an inner member having a mounting region located near its distal end for carrying the medical device, such as a stent, stent-graft and the like. The proximal region of the single wire generally has a circular cross-section and is coupled to the handle.

An outer catheter member is coaxially disposed over at least a portion of the inner member and includes a retraining sheath adapted to cover the medical device. The retraining sheath is movable by the control handle. An inner guide wire lumen formed, for example, from a length of flexible tubing, extends proximally from the distal end of the inner member. This guide wire lumen can be partially or totally connected directly to the flat wire portion of the inner member. The flat wire portion of the inner member provides a solid structure for connecting the guide wire lumen to the inner member. This guide wire lumen has a first opening spaced apart from a second opening which can be located along the distal region of the inner member. In another aspect of the present invention, shrink wrapping can be used to wrap the flat wire portion of the inner member and the guide wire lumen together.

In one aspect of the present invention, a distal tip is coupled to the inner member by utilizing the flat wire portion of the inner member. In one aspect, the distal tip includes a bonding port extending through the wall of the distal tip to an inner lumen formed therein. This bonding port extends from the outer surface of the distal tip to the surface of the flat wire when the distal tip is to be attached to the inner member. This bonding port is adapted to receive a bonding material which fixedly attaches the distal tip to the flat wire portion. This structure allows for the simple and quick assembly of the distal tip to the inner member.

In one aspect, the shrink wrap used to connect the guide wire lumen to the flat wire portion is removed at the location where the bonding port overlies the flat wire portion. This structure allows the distal tip to be bonded directly to the surface of the flat wire portion to create a strong bond between these components. In an alternative embodiment, the shrink wrap extends entirely over the flat wire portion so that the bonding port is directly over the shrink wrap which surrounds the flat wire portion. The distal tip would then be bonded directly to the shrink wrap tubing, rather than directly to the surface of the flat wire portion.

In yet another aspect, the inner member includes a proximal section having a circular diameter which extends proximally from the flat wire portion. The single wire transitions from a circular diameter to the flat wire portion near the second opening of the guide wire lumen. The outer catheter member may include a guide wire opening located near the second opening of the guide wire lumen to allow a guide wire to extend therethrough. In this fashion, a "rapid-exchange" type delivery system can be attained.

In another aspect of the present invention, the handle includes a tubular support member having a distal end and a proximal end with a lumen extending therethrough. The proximal region of the inner member (single wire) is adapted to extend through the lumen and is attached to the proximal end of the tubular member to secure the inner member to the handle. A luer fitting could be utilized to attach the end of the tubular member and inner member to the handle.

These and other features of the present invention become apparent from the following detailed description and the accompanying exemplary drawings.

BRIEF DESCRIPTION OF THE DRAWINGS

FIG. 2B is a cross-sectional view of the catheter portion taken along line 2B-2B;

FIG. 2C is an exploded view of the catheter portion of the system along line 2C;

FIG. 2D is a cross-sectional view of the catheter portion taken along line 2D-2D;

DETAILED DESCRIPTION OF THE PREFERRED EMBODIMENTS

The present invention relates to a system that delivers and deploys a medical device at a target site within a patient's body, such as a body lumen. For illustration purposes, the following exemplary embodiments are directed to a system for delivering and deploying a self-expanding stent, although it is understood that the present invention is applicable to other medical devices which are implantable in a body lumen as well as other parts of the body. Additionally, the medical device can be either a self-expanding device or a non self-expanding device.

Figure 1:
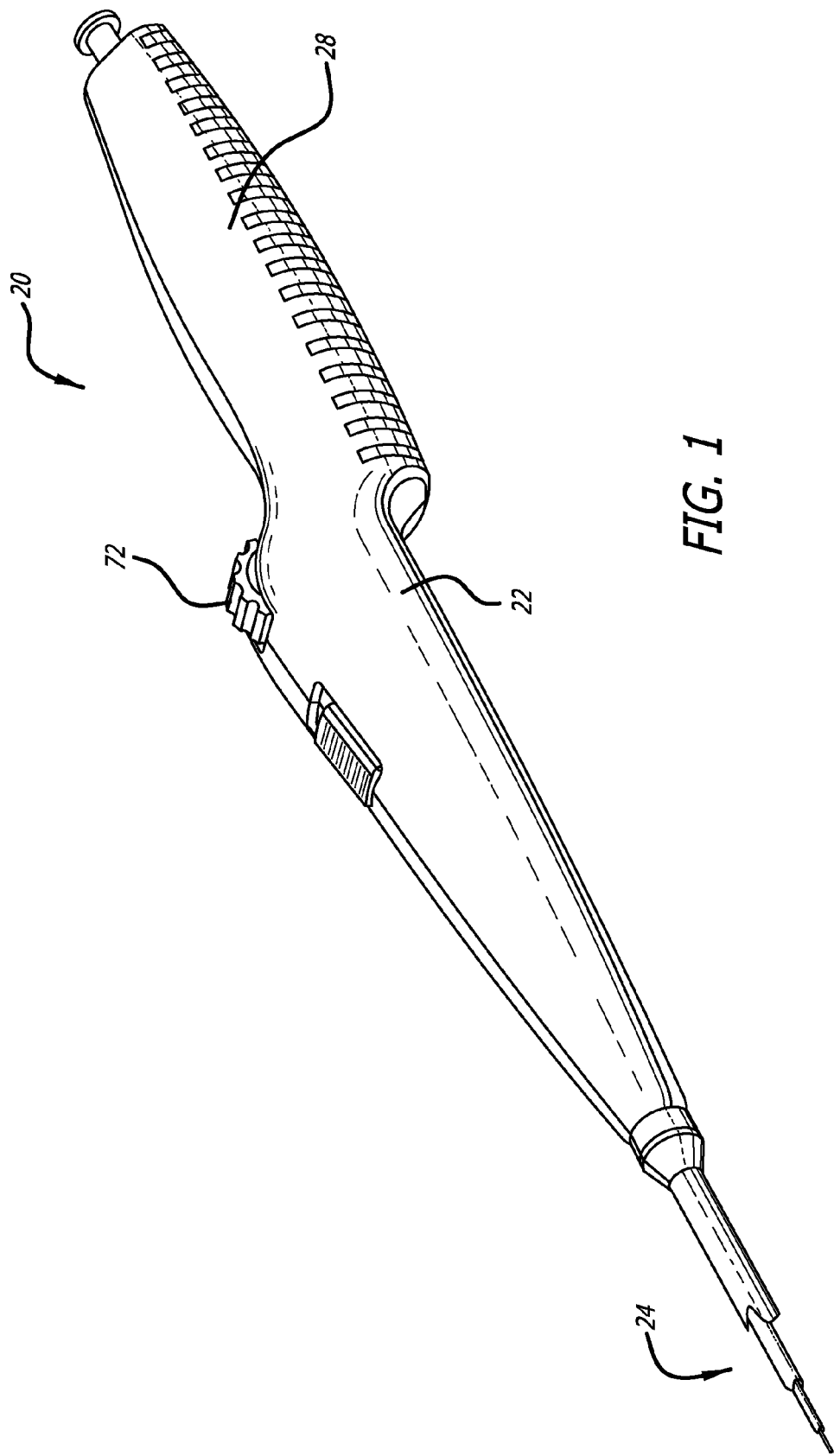
FIG. 1 is a perspective view of an embodiment of a delivery system incorporating features of the present invention.
Figure 2A:
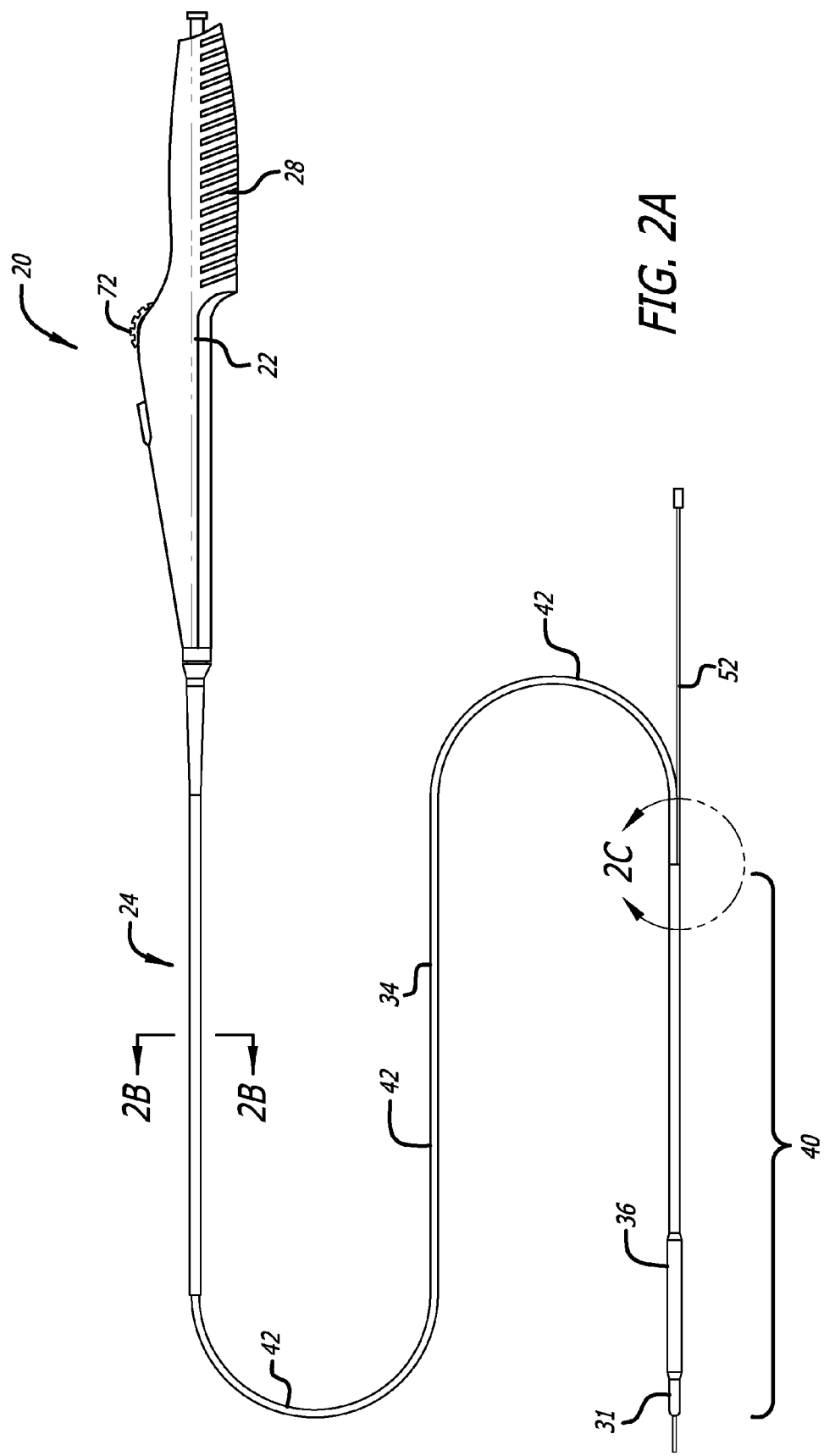
FIG. 2A is a side, elevational view of the embodiment of a delivery system of FIG. 1 including the catheter portion which extends from the deployment handle.

Referring now to FIGS. 1-5, a delivery system 20 incorporating features of the present invention is illustrated. The delivery system 20 includes a handle 22 with a catheter portion 24 coupled to the handle 22. A medical device, such as a stent 26 (FIG. 3A), is to be delivered by the delivery system 20 in a target sight within the patient's vasculature. As can be seen in FIGS. 1 and 2, the handle 22 includes a gripping portion 28 which allows the physician to grasp the handle and actuate the actuating mechanism associated with the handle.

The catheter portion 24 includes an inner member 30 which extends from the handle 22 to the distal end 31 of the catheter portion. This inner member 30 is made from a single, continuous wire having unique features to help reduce the overall profile of the catheter portion 24. The inner member 30 has a device mounting region 32 locating near the distal end 31 of the catheter portion 24, upon which the stent 26 is mounted in a delivery position. An outer catheter member 34, including a restraining sheath 36, is coaxially disposed over the inner member 30. In this particular embodiment, the restraining sheath 36 is designed to extend over the entire stent 26 to maintain the stent in a collapsed, delivery position. An actuating mechanism 38, which includes a rotatable thumbwheel, can be rotated by the physician to retract the outer catheter member 34 and the restraining sheath 36 from the stent 26 to allow the stent to self expand into its fully expanded position.

The inner member 30 includes a distal region 40 and a proximal region 42 which extends substantially the entire length of the catheter portion 24. This distal region 40 of the inner member 30 includes a flat wire portion 44 in which the inner member has a flat or ribbon shape to create a "support" structure which allows for the quick and easy assembly of components parts together. The advantages of this flat-wire portion 44 will be described in greater detail below. The inner member 30 has a generally round or circular diameter in the proximal region 42. The diameter of the single wire in the proximal region 42 is sufficient to provide the needed axial strength to allow the catheter portion of the system to be pushed up along a guide wire into a target location in the patient's vasculature. The proximal region 42 of the inner member 30 can include transition regions where the diameter of the wire decreases in a proximal to distal fashion. Therefore, the single wire forming the inner member can have a smaller diameter near its distal region where more flexibility is needed and a larger diameter in a proximal portion where more strength may be needed to provide adequate pushability to the catheter portion 24 of the delivery system 20.

A distal tip 46 is attached to the flat wire portion 44 of the inner member 30. This distal tip 46 provides a soft, atraumatic component to the catheter portion 24 to help prevent a "snow plowing" effect as the distal end of the catheter portion is delivered through the patient's vasculature. The delivery system 20 includes a guide wire lumen 48 which can be made, for example, from a length of flexible tubing. This guide wire lumen 48 is attached directly to the flat wire portion 44 of the inner member 30. This guide wire lumen 48 includes a first opening 50 located at the distal end of the tubing and a second opening 51 which extends along the length of the flat wire portion 44 to provide egress for a guide wire 52. This guide wire lumen 48 thus provides a short segment which allows the catheter portion 24 to ride along the guide wire 52. As can be see in FIGS. 3A, 3B and 3C, shrink wrap 54 can be utilized to attach the guide wire lumen 48 to the flat wire portion 44. It will be appreciated those skilled in the art that other means for attaching the guide wire lumen 48 to the flat wire portion 44 could be utilized. For example, adhesives, crimping rings and similar fastening devices could be utilized as well.

The outer catheter member 34 also includes a guidewire opening 56 which allows the guidewire 52 to exit the guide wire lumen 48 and the outer catheter member 34. As can be seen in FIG. 2C, a short segment 53 of the guide wire lumen 48 is not encased by the shrink wrap 54 near the second opening 51 to allow the segment 53 to be easily positioned within the guide wire opening 56 of the outer catheter member 34. This construction allows the guide wire lumen 48 to be easily aligned with the opening 56 during manufacturing. In use, the outer catheter member 34 is simply retracted proximally while the guide wire 52 remains in the guide wire lumen 48. The guide wire 52 also extends through a lumen 58 formed within the distal tip 46. Again, the atraumatic distal tip 46 helps to prevent trauma to the vessel wall as the catheter portion 24 is being advanced along the guidewire.

Generally, in a vascular procedure, a guide wire 52 has already been implanted in the patient's vasculature and the delivery system 20 is advanced over the implanted guide wire. This guide wire lumen 48 provides what is known as a rapid-exchange feature to the delivery system so that only the guide wire lumen actually slides over the guide wire, to help reduce the amount of friction between the catheter portion 24 and the guide wire 52.

Figure 3A:
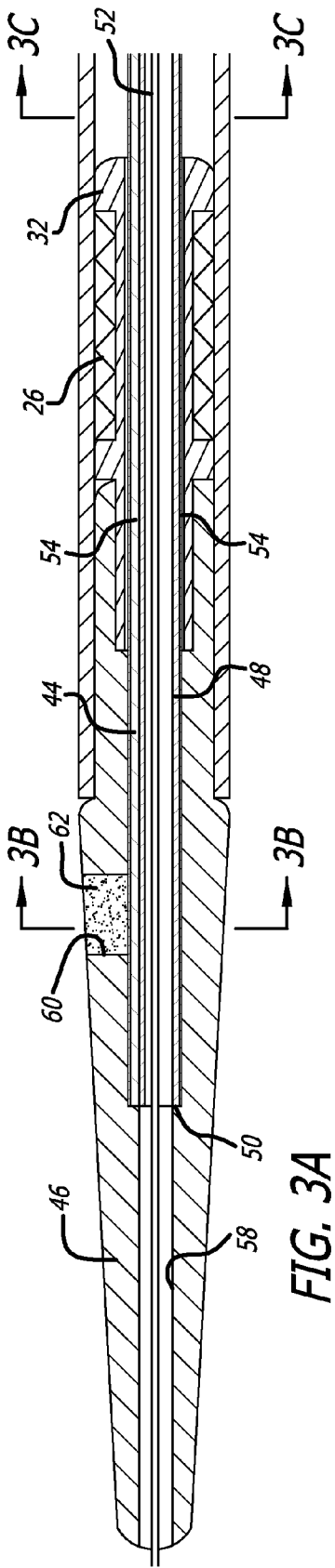
FIG. 3A is a cross sectional view of the distal portion of the delivery system of FIG. 1.
Figure 3C:
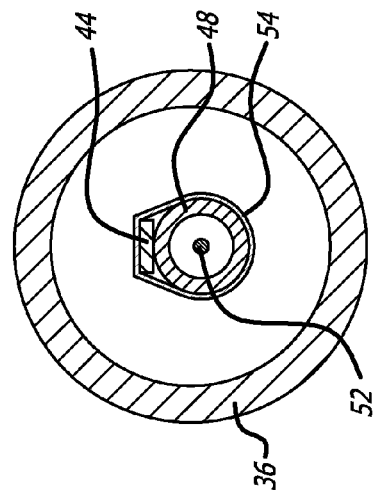
FIG. 3C is a cross sectional view of the distal portion of the delivery system of FIG. 3A taken along line 3C-C.
Figure 3B:
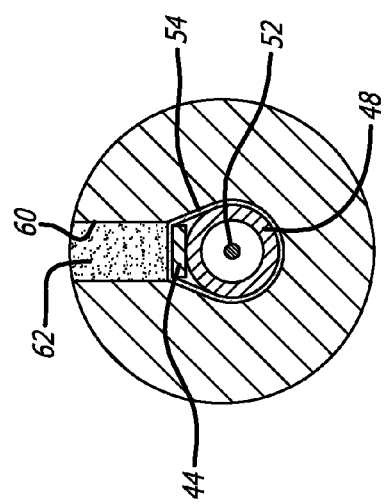
FIG. 3B is a cross sectional view of the distal portion of the delivery system of FIG. 3A taken along line 3B-3B.
Figure 4:
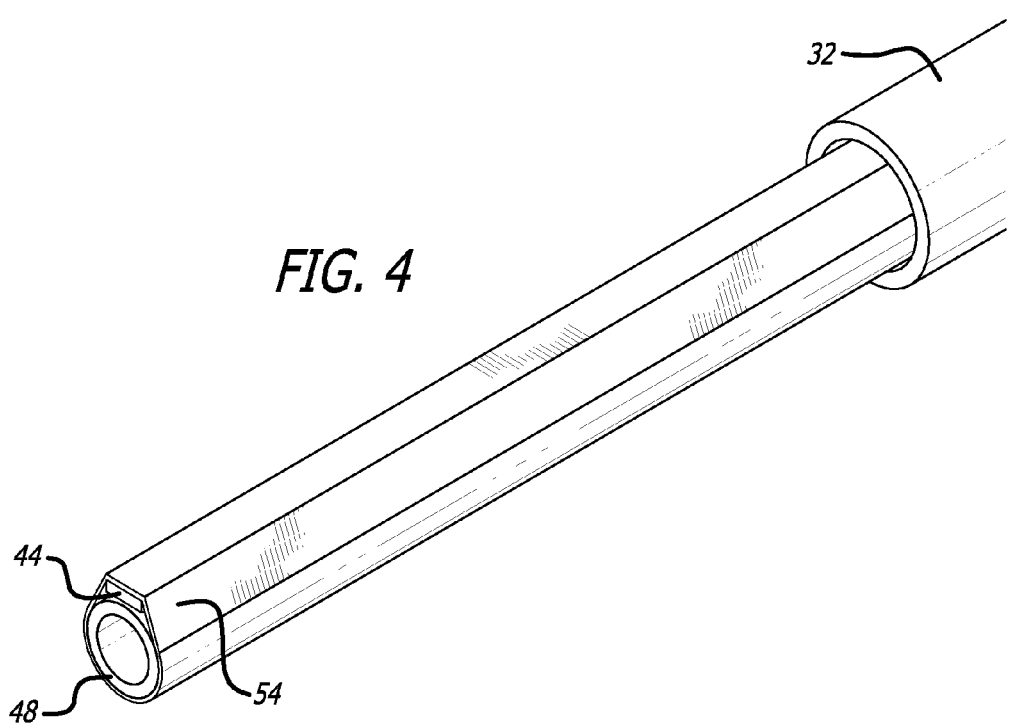
FIG. 4 is a perspective view of a distal end of a delivery system incorporating features of the present invention.
Figure 5:
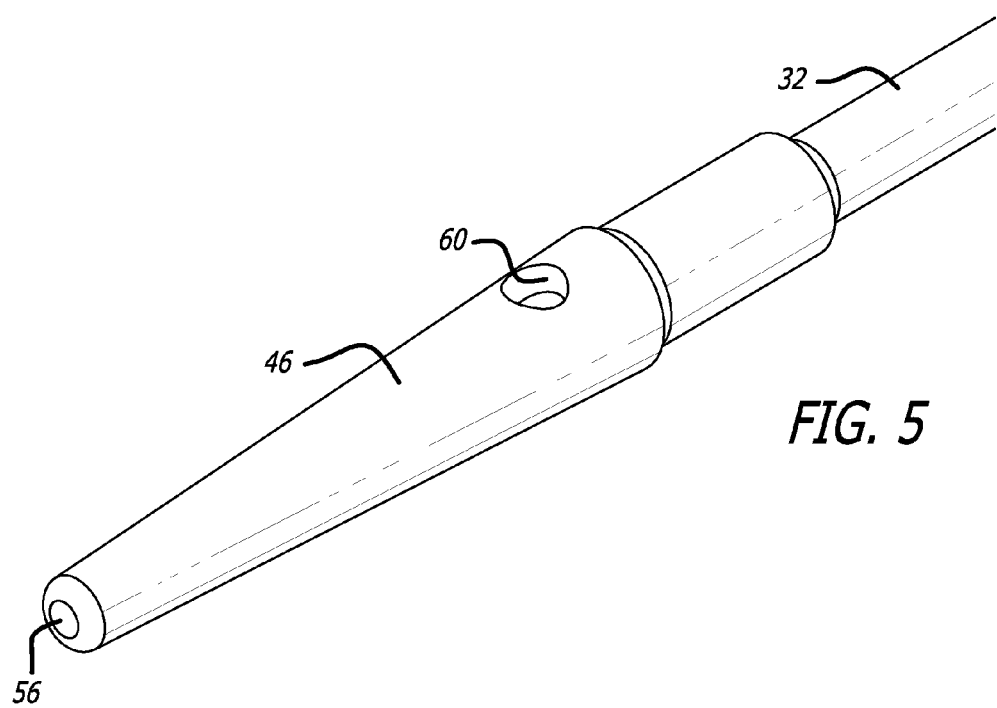
FIG. 5 is a perspective view of the distal end shown in FIG. 4 with an attached tapered tip component.

Referring specifically now to FIG. 5, the distal tip 46 is shown including a bonding port 60 which extends through the wall of the distal tip 46 into the lumen 58. This bonding port 60 is adapted to receive a bonding material, such as an adhesive 62 (see FIGS. 3A and 3B) which couples the distal tip 46 to the flat wire portion 44 of the inner member 30. As can be seen in FIGS. 3A and 3B, in this particular embodiment, the adhesive material 62 actually bonds directly to the shrink wrap 54 which encases both the flat wire portion 44 and the guide wire lumen 48. From a manufacturing standpoint, this bonding port 60 makes it quite easy to bond the distal tip 46 to the inner member 30 by using the flat wire portion 44. This structure provides for easy set up since adhesive material 62 can be easily applied to achieve tip bonding. It should still be appreciated that other portions of the distal tip could also be bonded to other components, such as the guide wire lumen 48, as well, to increase the overall strength of the tip attachment. A suitable adhesive for bonding the components together is Loctite 4306 which is a flashcure cyanacrylate adhesive manufactured by Loctite.

Figure 6:
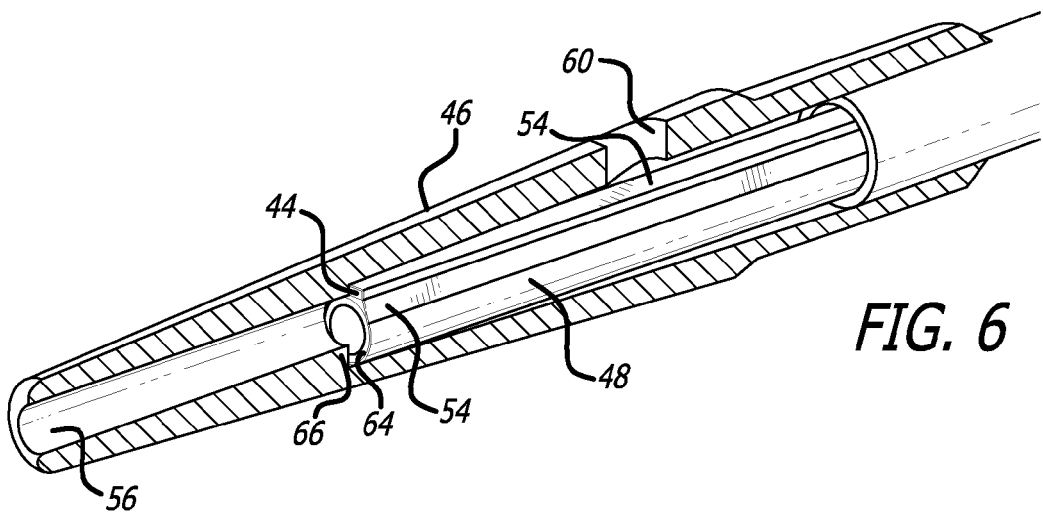
FIG. 6 is a perspective view partially in cross section of a distal end of a delivery system incorporating features of the present invention.

FIG. 6 shows the distal end 64 of a guide wire lumen 48 as it abuts against a shoulder 66 formed in the lumen 56 of the distal tip 46. As can be seen in FIG. 6, the distal most end of the flat wire portion 44 extends to the distal end 64 of the guide wire lumen 48. Other variations regarding the location of the distal end 64 of the guide wire lumen 56 will be discussed in greater detail.

Figure 7:
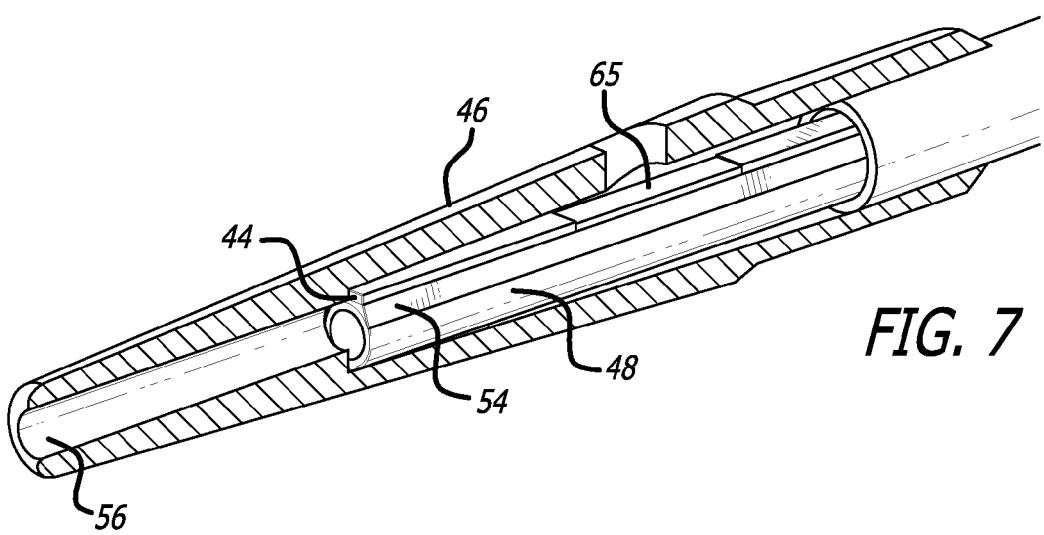
FIG. 7 is a perspective view, partially in cross section, of the distal end of a delivery system shown in FIGS. 3A, 3B, 3C, 4 and 5.

FIG. 7 shows an alternative structure which allows the distal tip 46 to be directly attached to surface of the flat wire portion 44 of the inner member 30. In this particular embodiment, a portion of the shrink wrap 54 has been removed to expose the surface of the flat wire portion 44. This exposed region 65 of the flat wire portion 44 would be located directly beneath the bonding port 60 so that the adhesive (not shown in FIG. 7) will come in direct contact with the surface of the flat wire portion 44, rather than the shrink wrap 54, as is shown in the previous embodiment. This particular embodiment of the present invention is desirable since it creates an extremely strong bond between the distal tip 46 and the flat wire portion 44 of the inner member 30.

Figure 8:
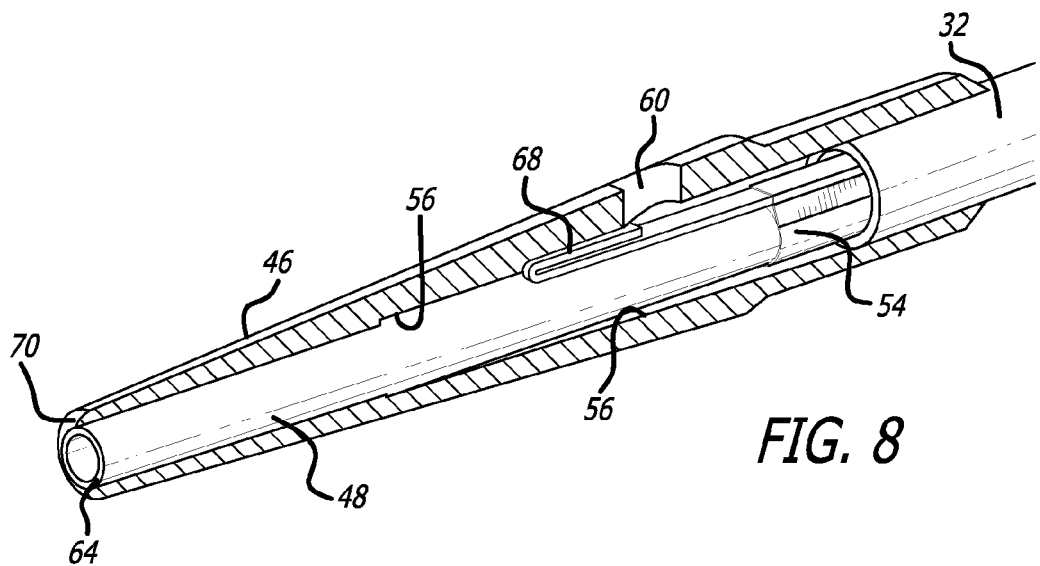
FIG. 8 is a perspective view, partially in cross section, of the distal end of a delivery system incorporating features of the present invention.

Referring now to FIG. 8, another alternative embodiment is shown in which the distal most end 68 of the flat wire portion 44 bents over a portion of itself in the area near the bonding portion 60. The distal end 68 is bent over itself in order to take up any space which may exist between the lumen 58 of the distal tip 46 and the flat wire portion and guidewire lumen 48. In this particular embodiment, the flat wire portion 44 is again fully exposed to allow the application of the adhesive material (not shown) to bond directly onto the surface of the flat wire portion 44 rather than the shrink wrap 54. Shrink wrap 54 is still used in the particular embodiment, however, it terminates just proximal to the bonding port 60, as is shown in FIG. 8. Also, as can be seen in FIG. 8, the distal end 64 of the guide wire lumen 48 is shown extending all the way to the distal most end 70 of the distal tip 46

Figure 9:
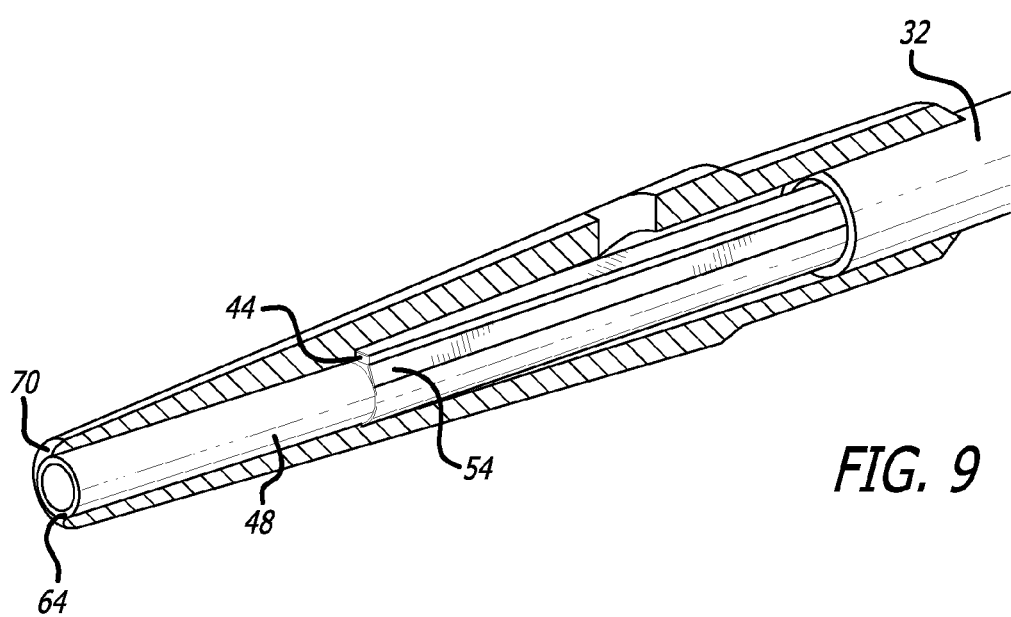
FIG. 9 is a perspective view, partially in cross section, of the distal end of a delivery system incorporating features of the present invention.

Referring now to FIG. 9, still another embodiment of the present invention is shown with the distal end 64 of the guide wire lumen 48 extending fully to the distal most end 70 of the distal tip 46. This particular embodiment is very similar to the one shown in FIG. 6 except for the fact that the guide wire lumen 48 now extends fully through to the distal most end 70 of the distal tip 46. It should be appreciated that this particular embodiment shown in FIG. 9 can also have a configuration in which a portion of the shrink wrap 54 is removed directly under the bonding port 60 to allow the adhesive to bond directly onto the surface of the flat wire portion 44 of the inner member 30.

Figure 10:
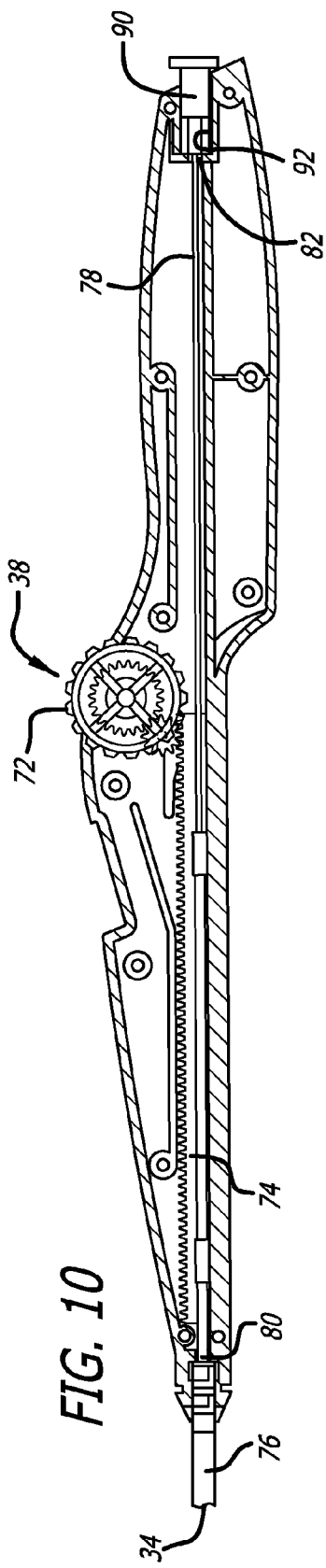
FIG. 10 is a cross sectional view of the delivery system of FIG. 1 showing other features of the present invention.
Figure 11:
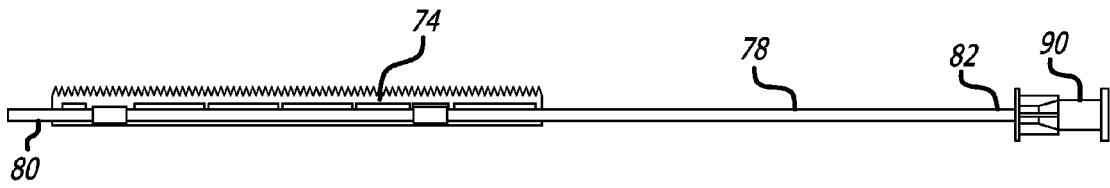
FIG. 11 is a side, elevational view of a portion of the actuation mechanism shown in FIG. 10.

Referring now to FIG. 10, the handle 22 is shown with the actuating mechanism 38 which causes the outer catheter member 34 and the restraining sheath 36 to be retracted proximally in order to remove the sheath 36 from the stent 26. The actuating mechanism includes a thumbwheel 72 which is operative connected with a rack-in-pinion assembly 74. The proximal end 76 of the outer catheter member 34 can be coupled to this rack-in-pinion assembly 74, as is shown in FIG. 10. When the physician manipulates the thumbwheel 72 in a clockwise rotation, the rack-in-pinion assembly 74 moves proximally causing the outer catheter member 34 and restraining sheath 36 to move proximally as well. The handle 22 is shown including a tubular support member 78 upon which the rack portion of the rack and gear assembly is mounted. This tubular support member 78 extends from the proximal end 80 to the distal end 82 of the handle 22. The proximal end 84 of the inner member 30 is designed to extend within a lumen 86 formed within this tubular member 78.

Figure 12:
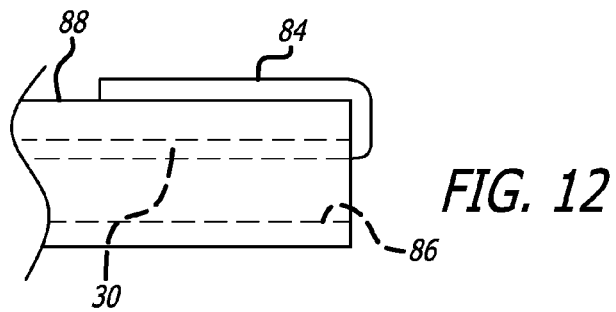
FIG. 12 is a side, elevational view of the proximal end of the component shown in FIG. 10 with the Luer valve removed.
Figure 13:
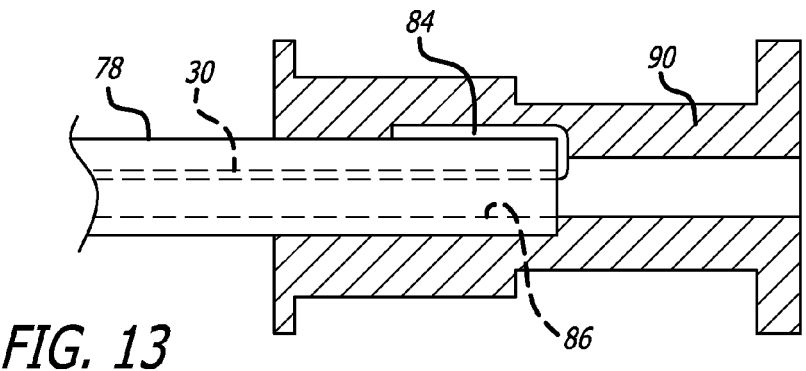
FIG. 13 is a cross sectional view of the Luer valve shown in FIG. 11.

As can be seen in FIG. 12, the proximal end 84 of the inner member 30 extends through this lumen 86 and is bent back against the outer surface 88 of the tubular member 78 to form a "hook" which helps to fasten the inner member 30 to the handle 22. A luer fitting 90, shown in FIG. 13, can be placed over the proximal end 84 of the tubular member 78, along with the proximal end 86 of the inner member 30, to securely fasten the inner member 30 onto the tubular member 78. This luer fitting 90 is, in turn, fastened within a recess 92 formed at the proximal end 80 of the handle. In this fashion, the inner member 30 will remain securely attached to the handle 22. It should be appreciated that the present embodiment shows just one manner in which the proximal end of the inner member 30 can be attached to a handle portion. Additionally, one particular handle is shown for purposes of explaining the present invention. It should be appreciated that other styles of handles could be used with the inner member described above.

The catheter components such as the outer tubular members and guide wire lumen can be formed of materials found useful in catheter construction. For example, the polymeric tubular members can be formed of materials such as polyamides (e.g., nylon), polyamide copolymers (e.g., polyether block amide), polyolefins (e.g., polyethylene), polyurethanes, polyesters, and the like. Generally speaking, the more proximal portions of the outer tubular member are usually stiffer than the distal portions, to provide the catheter sufficient pushability, and the catheter distal section is configured to provide flexibility and trackability to advance through the patient's vascular system by tracking on the guide wire. However, since a wire is utilized to create the inner member 30, the strength of the catheter portion can be more strongly associated with the wire, than the other portion. Therefore, the diameter and stiffness of the outer member and restraining sheath can be decreased due to the increased strength supplied by the inner member 30.

The wire forming the inner member 30 must have sufficient strength for the intended application. It will be understood that different strength material could be used for particular applications. The inner member 30 can be made from high strength metals and alloys, such as, for example, stainless steel, high tensile stainless steel such as hi-ten 304V, precipitation hardenable alloys, including precipitation hardenable stainless steel and other high strength alloys such as MP35N, L605, Elgiloy and metallic and high strength polymeric materials associated with medical grade devices. The inner member 30 may also be made from superelastic, pseudoelastic or shape memory alloys such as NiTi. High strength alloys used with medical grade devices can also be used. Also, the size of the diameter of the proximal portion of the wire can vary. It has been found that stainless steel wire having a diameter of about 0.012 to 0.014 inches is suitable. Larger diameter wires, e.g. up to 0.035 inch (0.89 mm) or more may be employed when the delivery device is to be used in peripheral arteries and other body lumens. The flat wire portion 44 can have generally rectangular shaped transverse cross-sections which usually have dimensions of about 0.008 to about 0.014 inches (0.2-0.36 mm) in width and about 0.0004 to about 0.008 inches (0.1-0.2 mm) in thickness. It should be appreciated that the width and thickness of the flat wire portion can be varied, as needed for a particular application. The above-listed ranges of widths and thickness have been found to provide sufficient flexibility for a delivery system to be used in a vascular system. However, these dimensions can vary, of course, depending upon the type of material chosen to create the inner member.

The overall length of the inner member 30 and the length of the flat wire portion 44 also will vary depending upon the procedure. For most percutaneous intravascular procedures, the overall length of the inner member would be generally about 100 to about 200 cm. The length of the distal flat wire portion 44 can range from about 5 to about 30 cm, depending upon the flexibility and other properties desired in the final product.

The inner member can be coated with a lubricious coating such as a fluoropolymer, e.g. TEFLON® available from DuPont, MICROGLIDE™ coating and other commercially available coatings which extends the length of the proximal section of the inner member 30. A hydrophilic coating may also be employed. These coating help to reduce friction between the surface of the inner member 30 and the inner surface of the outer catheter member 34.

It is to be understood that even though numerous characteristics and advantages of the present invention have been set forth in specific description, together with details of the structure and function of the invention, the disclosure is illustrative only and changes may be made in detail, such as size, shape and arrangement of the various components of the present invention, without departing from the spirit and scope of the present invention. It would be appreciated to those skilled in the art that further modifications or improvement may additionally be made to the delivery system disclosed herein without departing from the scope of the invention. Accordingly, it is not intended that the invention be limited, except as by the appended claims.

I claim:

1. A system for delivering and deploying a medical device within a patient, the system comprising:
    a medical device;
    a control handle;
    a catheter portion coupled to the control handle, the catheter portion including an inner member having a mounting region located near its distal end for carrying the medical device, the inner member being made from a single wire having a flat wire portion at a distal region and a proximal region coupled to the handle, an outer catheter member coaxially disposed over at least a portion of the inner catheter member, the outer catheter member including a restraining sheath adapted to cover the medical device, the retraining sheath being movable by the control handle;
    an inner guide wire lumen formed from a length of tubing extending proximally from the distal end of the inner member, the guide wire lumen having a first opening spaced apart from a second opening extending along the distal region of the inner member;
    a distal tip fixedly attached directly to the flat wire portion of the inner member, the distal tip being mounted on the inner guide wire lumen;
    wherein the flat wire portion of the inner member overlays at least a portion of the inner guide wire lumen and extends to the distal tip.

2. The system of claim 1, wherein the distal tip includes a first portion adapted to extend over the flat wire portion and the guide wire lumen and a bonding port extending through the distal tip, the bonding port extending through the wall of the distal tip to the surface of the flat wire, the bonding port adapted to receive a bonding material which bonds the distal tip to the flat wire portion.

3. The system of claim 2, wherein the first portion of the distal tip is a tubular member having a lumen for receiving the guide wire lumen and the flat wire portion of the inner member, the distal tip including a second portion adjacent to the first portion forming a distally tapering portion.

4. The system of claim 3, wherein the bonding port is located at the second portion of the distal tip.

5. The system of claim 1, further including a shrink wrap tubing extending over the flat wire portion of the inner member and the guide wire lumen to attach the inner member to the guide wire lumen.

6. The system of claim 5, wherein the shrink wrap does not extend over the flat wire portion of the inner member at the location where the bonding port overlies the flat wire portion.

7. The system of claim 5, wherein the shrink wrap extends over the flat wire portion of the inner member at the location where the bonding port overlies the flat wire portion to allow the bonding material to bond directly to the exposed surface of the shrink wrap tubing.

8. The system of claim 1, wherein the distal end of the flat wire portion is bent back unto itself within the lumen of the distal tip.

9. The system of claim 1, wherein the outer catheter member includes a guide wire opening along its length located adjacent to the second opening of the guide wire lumen.

10. The system of claim 9, wherein a guide wire is adapted to extend through the second opening of the guide wire lumen and through the guide wire opening in the outer catheter member.

11. The system of claim 9, wherein the inner member has a proximal section having a circular diameter located proximate to the flat wire portion and the transition from the proximal section to the flat wire portion is near the second opening of the guide wire lumen.

12. The system of claim 11, wherein the proximal section of the inner member includes transition regions having different diameters.

13. The system of claim 1, wherein the tubing forming the guide wire lumen extends to the distal end of the distal tip.

14. The system of claim 1, wherein the tubing forming the guide wire lumen has a distal end which terminate proximate to the distal end of the distal tip.

15. The system of claim 1, wherein the handle includes a tubular member having a distal end and a proximal end with a lumen extending therethrough and the proximal region of the inner member extends through the lumen and is attached to the proximal end of the tubular member.

16. The system of claim 15, further including a luer fitting attached to the proximal end of the tubular member and the inner member.

17. The system of claim 1, wherein the flat wire portion extends along the guide wire lumen at a position proximal to the medical device to a position distal to the medical device.

* * * * *